United States Patent
Li et al.

(10) Patent No.: US 9,914,711 B2
(45) Date of Patent: Mar. 13, 2018

(54) BACTERIAL QUORUM SENSING REGULATOR AND MEDICAL USE THEREOF

(71) Applicant: Institute of Pharmacology and Toxicology Academy of Military Medical Sciences P.L.A. China, Beijing (CN)

(72) Inventors: Song Li, Beijing (CN); Junhai Xiao, Beijing (CN); Mingming Zhao, Beijing (CN); Wu Zhong, Beijing (CN); Lili Wang, Beijing (CN); Zhibing Zheng, Beijing (CN); Yunde Xie, Beijing (CN); Xingzhou Li, Beijing (CN); Guoming Zhao, Beijing (CN); Xinbo Zhou, Beijing (CN); Xiaokui Wang, Beijing (CN); Wei Chen, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 14/766,466

(22) PCT Filed: Dec. 10, 2013

(86) PCT No.: PCT/CN2013/088940
§ 371 (c)(1),
(2) Date: Aug. 7, 2015

(87) PCT Pub. No.: WO2014/121634
PCT Pub. Date: Aug. 14, 2014

(65) Prior Publication Data
US 2016/0002184 A1  Jan. 7, 2016

(30) Foreign Application Priority Data
Feb. 8, 2013  (CN) .......................... 2013 1 0050051

(51) Int. Cl.
C07D 263/26 (2006.01)
A61K 31/421 (2006.01)
A61K 45/06 (2006.01)

(52) U.S. Cl.
CPC .......... *C07D 263/26* (2013.01); *A61K 31/421* (2013.01); *A61K 45/06* (2013.01)

(58) Field of Classification Search
CPC .................................................. C07D 263/26
See application file for complete search history.

(56) References Cited

U.S. PATENT DOCUMENTS 3,141,889 A  7/1964  Ebetino
4,032,638 A  6/1977  Wah Wat

FOREIGN PATENT DOCUMENTS

WO  WO 2006/084056 A2  8/2006

OTHER PUBLICATIONS

Milcent, et al. Document No. 120:298521, retrieved from CAPLUS, (1994).*
Zhelyazkvov, et al. Document No. 79:31640, retrieved from CAPLUS, (1972).*
Wat. Document No. 87:102350, retrieved from CAPLUS, (1984).*
Cervi, et al. Document No. 64:104142, retrieved from CAPLUS, (1966).*
Staph Infection [online] {retrieved on Apr. 10, 2008 from the Internet} {URL: http://www.medicinenet.com/script/main/art.asp?articlekey=1991&pf=3&page2}.*
Salmonellosis [online] [retrieved on Feb. 27, 2009] and retrieved from URL; http://www.cdc.gOv/nczved/dfbmed/disease_listing/salmonellosis_gi.html#4.*
Staph Infection [online] {retrieved on May 3, 2017 from the Internet} {URL: http://www.medicinenet.com/staph_infection/page8.htm.}.*
Amara, N. et al., "Covalent Inhibition of Bacterial Quorum Sensing," *JACS* 131(5):10610-10619, American Chemical Society, United States (2009).
Database Registry, *Chemical Abstracts Service*, Columbus Ohio, Access No. 65043-10-9, United States (1984).
Reverchon, S. et al., "New Synthetic Analogues of N-Acyl Homoserine Lactones as Agonists or Antagonists of Transcriptional Regulators Involved in Bacterial Quorum Sensing," *Bioorg. Med. Chem. Lett.* 12:1153-1157, Elsevier Science Ltd., England (2002).
Cervi, F.R., et al., "The Preparation and Attempted Polymerization of Some 3-(Substituted Amino)-2-oxazolidinones," *J Org. Chem.* 31(2):631-632, American Chemical Society, United States (1966).
El-Zahraa, F., et al., "Synthesis and Pharmacological Screening of Certain N-Substituted Amides Structurally Related to Some Local Anesthetics," *Pharmazie* 34(1):12-13, abstract only, Verlag, Germany (1979).
International Search Report for International Application No. PCT/CN2013/088940, mailed from the State Intellectual Property Office of the P.R. China on Mar. 20, 2014, China.

(Continued)

*Primary Examiner* — Shawquia Jackson
(74) *Attorney, Agent, or Firm* — Sterne, Kessler, Goldstein & Fox P.L.L.C.

(57) ABSTRACT

The invention relates to a compound of formula I, and a preparation method and use thereof. The compound has a bacterial quorum-sensing regulatory effect, and can be used for prevention and/or treatment of a disease caused by a bacterial infection.

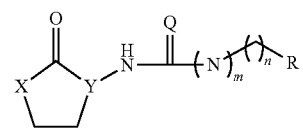

16 Claims, No Drawings

(56) References Cited

OTHER PUBLICATIONS

Milcent, R., et al., "Synthesis of 3-Acylamino-2-oxazolidinone Derivatives Through Cyclic Transformations of 5-Aryl (or Benzyl)-1,3,4-oxadiazol-2(3H)-one Derivatives," *Journal of Heterocyclic Chemistry* 30(4):905-908, Wiley-Blackwell, United States (1993).
Schaefer, A.L., et al., "Quorum Sensing in *Vibrio fischeri*: Probing Autoinducer-LuxR Interactions with Autoinducer Analogs," *J Bacteriol.* 178(10):2897-2901, American Society for Microbiology, United States (1996).
Soliman, L.N., et al., "Synthesis of some N-substituted salicylamides structurally related to certain antimicrobials," *Die Pharmazie* 32(6):323-325, Govi-Verlag Pharmazautischer Verlag, Germany (1977).

\* cited by examiner

BACTERIAL QUORUM SENSING REGULATOR AND MEDICAL USE THEREOF

TECHNICAL FIELD

The invention belongs to medical and chemical engineering field, specifically relates to design and synthesis as well as medical use of a new bacterial quorum-sensing regulator.

BACKGROUND ART

Bacteria communicate with each other by small auto-generated signal molecules, which are termed as auto inducers (AIs in brief). During the growth of bacterial quorum, these auto inducers are produced continuously and are subsequently secreted in the extracellular environment. When the concentration of the signal molecules reaches a threshold value, the expression of relevant genes in bacteria is initiated to adapt to the environmental changes. Such a regulatory system is termed as bacterial quorum sensing (QS) signal systems. QS enables unicellular bacteria to imitate multicellular organisms to accomplish some behaviors that can not be accomplished when they are unicellular individuals.

In 1970, Nealson et al. discovered QS in *V. fischeri* for the first time, i.e. when bacteria reached a high population concentration, the bacteria generated bioluminescence. In deep study on *V. fischeri*, N-acyl homoserine lactones (AHL) synthesized from LuxI protein activate lux operon of *V. fischeri* by interaction with transcription activating factor luxR. Similar regulatory systems were found in many Gram-positive or Gram-negative bacteria. Their mechanism lies in that when bacteria are at a low population density, the auto inducers synthase gene is expressed at a basic level, resulting in a small amount of autoinduction signal molecules, which are diffused extracellularly and are diluted immediately in the surrounding environment. When the population density of bacteria increases gradually and reaches a threshold value, the autoinduction signal molecules will be permeated into cells and bind to transcriptional regulatory proteins to form a transcriptional regulatory protein-signal molecule polymer, which can bind to a specific DNA sequence of the signal molecule in chromosome to enable the expression of target genes including the synthetic gene of the signal molecule, also resulting in the production of more signal molecules. Such communication and transduction of information among bacteria has been proposed for a long time. However, systematic research is only conducted in the recent 10 years. Such a phenomenon has been demonstrated to be present in many bacteria. For example, *chromobacterium violaceum* has the same mechanism as *V. fischeri*, and can produce C6-HSL as an auto induction molecule, the receptor protein of which is CviR.

Bacterial quorum sensing enables the regulation of expression of some relevant genes in a population of bacteria, such as regulation of generation of antibiotics, bioluminescence, regulation of nitrogen-fixing gene, conjugal transfer of Ti plasmid, expression of virulent gene, pigment generation, bacterial swarming, formation of biofilms, and the like. In the late 1970s, scientists found that naturally occurring or artificially synthesized bacterial quorum-sensing regulators (including agonists or inhibitors) can interfere with the transduction of signaling system and regulate the expression of adverse gene in bacteria.

Bacterial quorum-sensing regulators do not interfere with normal physiological functions of cells in vivo, and thus are regarded as new direction for the development of antibacterials. Bacterial quorum-sensing inhibitors can be used in combination with antibiotics to enhance sensitivity of pathogenic bacteria to antibiotics, and can be used to treat a disease (including, but not limited to peritonitis, cholecystitis, cystitis, diarrhea, endocarditis, gastroenteritis, pyothorax, sepsis and other various diseases) caused by a Gram-negative bacterium including, but not limited to *E. coli, Bacillus proteus, Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shigella* spp., *Pasteurella, Vibrio cholerae*, and *Vibrio Parahemolyticus*, particularly, to treat a disease caused by drug-resistant Gram-negative bacteria not sensitive to current antibiotics.

The purpose of the invention is to synthesize new bacterial quorum-sensing regulator, for use in the treatment of a disease caused by a Gram-negative bacterium, particularly a disease caused by drug-resistant Gram-negative bacteria.

CONTENTS OF INVENTION

In the first aspect, the invention provides a compound of Formula I, a racemate or optical isomer, a pharmaceutically acceptable salt, a solvate, or a hydrate thereof,

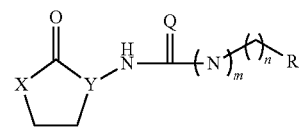

wherein,
X is O; Y is N; Q is O or S;
m is 0 or 1;
n is an integrate of from 0 to 9, preferably an integrate of from 0 to 8;
R is hydrogen, cyclohexyl, substituted or unsubstituted phenyl ring; wherein the phenyl ring is optionally mono-substituted or multi-substituted by a substituent selected from the group consisting of: substituted or unsubstituted C1-C5 linear or branched alkyl, halogen, cyano, trifluoromethyl, hydroxyl, nitro, and substituted or unsubstituted C1-C5 alkoxyl.

Preferably, in the compound of Formula I, a racemate or optical isomer, a pharmaceutically acceptable salt, a solvate, or a hydrate thereof,
when X is O, Y is N, and Q is O,
m is 0,
n is an integrate of from 0 to 9, preferably an integrate of from 0 to 8, or an integrate of from 0 to 3,
R is a substituted or unsubstituted phenyl ring; wherein the phenyl ring is optionally mono-substituted or multi-substituted by a substituent selected from the group consisting of: substituted or unsubstituted C1-C5 linear or branched alkyl, halogen, cyano, trifluoromethyl, hydroxyl, nitro, and substituted or unsubstituted C1-C5 alkoxyl; or
when X is O, Y is N, and Q is O or S,
m is 1,
n is an integrate of from 0 to 9, preferably an integrate of from 0 to 8,
R is hydrogen, cyclohexyl, substituted or unsubstituted phenyl ring; wherein the phenyl ring is optionally mono-substituted or multi-substituted by a substituent selected from the group consisting of: substituted or unsubstituted C1-C5 linear or branched alkyl, halogen, cyano, trifluoromethyl, trifluoromethoxyl, phenyl, hydroxyl, nitro, and substituted or unsubstituted C1-C5 alkoxyl.

More preferably, in the compound of Formula I, a racemate or optical isomer, a pharmaceutically acceptable salt, a solvate, or a hydrate thereof,
when X is O, Y is N, and Q is O,
m is 0,
n is 0, 1, 2 or 3,
R is substituted or unsubstituted phenyl ring, wherein the phenyl ring is optionally mono-substituted or multi-substituted by a substituent selected from the group consisting of: halogen, trifluoromethyl, methyl, chloromethyl, nitro, ethyl, n-propyl, iso-propyl, and methoxyl; or
when X is O, Y is N, Q is O or S,
m is 1, n is 0, 1, 2, 3, 4, 5, 6, 7, or 8,
R is hydrogen, cyclohexyl, substituted or unsubstituted phenyl ring, wherein the phenyl ring is optionally mono-substituted or multi-substituted by a substituent selected from the group consisting of: halogen, trifluoromethyl, methyl, chloromethyl, nitro, ethyl, n-propyl, iso-propyl, methoxyl, and trifluoromethoxyl.

In one embodiment of the invention, in the compound of Formula I, a racemate or optical isomer, a pharmaceutically acceptable salt, a solvate, or a hydrate thereof according to the first aspect of the invention, when X is O, Y is N, and Q is O, m is 0, n is 0-3, R is a substituted or unsubstituted phenyl ring, wherein the phenyl ring is optionally mono-substituted or multi-substituted by a substituent selected from the group consisting of: substituted or unsubstituted linear or branched alkyl, halogen, cyano, trifluoromethyl, hydroxyl, nitro, and alkoxyl; or when X is O, Y is N, and Q is O or S, m is 1, n is 0-3, R is substituted or unsubstituted C1-C9 linear alkyl, branched alkyl or cycloalkyl; or substituted or unsubstituted phenyl ring; wherein the phenyl ring is optionally mono-substituted or multi-substituted by a substituent selected from the group consisting of: substituted or unsubstituted linear or branched alkyl, halogen, cyano, trifluoromethyl, hydroxyl, nitro, and alkoxyl.

In one embodiment of the invention, in the compound of Formula I, a racemate or optical isomer, a pharmaceutically acceptable salt, a solvate, or a hydrate thereof according to the first aspect of the invention, when X is O, Y is N, and Q is O, m is 0, n is 0-3, R is phenyl, chlorophenyl, bromophenyl, fluorophenyl, nitrophenyl, cyanophenyl, methylphenyl, ethylphenyl, benzyl, trifluoromethylphenyl, methoxyphenyl, ethoxyphenyl, or halogenated methyl phenyl; or when X is O, Y is N, and Q is O or S, m is 1, n is 0-3, R is methyl, ethyl, propyl, butyl, pentyl, hexyl, cyclohexyl, heptyl, octyl, phenyl, chlorophenyl, bromophenyl, or methylphenyl.

In one embodiment of the invention, the compound of Formula I, a racemate or optical isomer, a pharmaceutically acceptable salt, a solvate, or a hydrate thereof according to the first aspect of the invention, is selected from the group consisting of:
4-fluoro-N-(2-oxo-oxazolidin-3-yl)benzamide (Compound 1);
4-tert-butyl-N-(2-oxo-oxazolidin-3-yl)benzamide (Compound 2);
4-chloromethyl-N-(2-oxo-oxazolidin-3-yl)benzamide (Compound 3);
2-chloro-N-(2-oxo-oxazolidin-3-yl)benzamide (Compound 4);
3-chloro-N-(2-oxo-oxazolidin-3-yl)benzamide (Compound 5);
2-fluoro-N-(2-oxo-oxazolidin-3-yl)benzamide (Compound 6);
4-nitro-N-(2-oxo-oxazolidin-3-yl)benzamide (Compound 7);
3-methyl-N-(2-oxo-oxazolidin-3-yl)benzamide (Compound 8);
4-fluoro-N-(2-oxo-oxazolidin-3-yl)benzamide (Compound 9);
2-trifluoromethyl-N-(2-oxo-oxazolidin-3-yl)benzamide (Compound 10);
4-ethyl-N-(2-oxo-oxazolidin-3-yl)benzamide (Compound 11);
4-bromo-N-(2-oxo-oxazolidin-3-yl)benzamide (Compound 12);
3-fluoro-N-(2-oxo-oxazolidin-3-yl)benzamide (Compound 13);
3-propyl-N-(2-oxo-oxazolidin-3-yl)benzamide (Compound 14);
1-(2-oxo-oxazolidin-3-yl)-3-butyl urea (Compound 15);
1-(2-oxo-oxazolidin-3-yl)-3-pentyl urea (Compound 16);
1-(2-oxo-oxazolidin-3-yl)-3-hexyl urea (Compound 17);
1-(2-oxo-oxazolidin-3-yl)-3-heptyl urea (Compound 18);
1-(2-oxo-oxazolidin-3-yl)-3-octyl urea (Compound 19);
1-(4-bromophenyl)-3-(2-oxo-oxazolidin-3-yl) urea (Compound 20);
1-(2-oxo-oxazolidin-3-yl)-3-p-tolylurea (Compound 21);
1-cyclohexyl-3-(2-oxo-oxazolidin-3-yl) urea (Compound 22);
1-benzyl-3-(2-oxo-oxazolidin-3-yl) urea (Compound 23);
1-(2-oxo-oxazolidin-3-yl)phenyl ethyl urea (Compound 24);
1-(2-oxo-oxazolidin-3-yl)-3-(m-tolyl) urea (Compound 25);
1-(3-bromophenyl)-3-(2-oxo-oxazolidin-3-yl) urea (Compound 26);
1-(2-oxo-oxazolidin-3-yl)phenylthiourea (Compound 27);
1-(4-fluorophenyl)-3-(2-oxo-oxazolidin-3-yl)sulfourea (Compound 28);
1-(3-bromophenyl)-3-(2-oxo-oxazolidin-3-yl) urea (Compound 29);
1-(2-oxo-oxazolidin-3-yl)-3-(4-trifluoromethoxyphenyl) urea (Compound 30);
2-(4-fluorophenyl)-N-(2-oxo-oxazolidin-3-yl)acetamide (Compound 31);
2-(4-methoxyphenyl)-N-(2-oxo-oxazolidin-3-yl)acetamide (Compound 32);
2-(4-nitrophenyl)-N-(2-oxo-oxazolidin-3-yl)acetamide (Compound 33);
2-(4-chlorophenyl)-N-(2-oxo-oxazolidin-3-yl)acetamide (Compound 34);
2-(4-tolyl)-N-(2-oxo-oxazolidin-3-yl)acetamide (Compound 35);
2-(4-nitrophenyl)-N-(2-oxo-oxazolidin-3-yl)propanamide (Compound 36);
2-(4-phenyl)-N-(2-oxo-oxazolidin-3-yl)propanamide (Compound 37);
2-(4-methylphenyl)-N-(2-oxo-oxazolidin-3-yl)propanamide (Compound 38);
2-(4-chlorophenyl)-N-(2-oxo-oxazolidin-3-yl)propanamide (Compound 39); and
N-(2-oxo-oxazolidin-3-yl)-4-phenyl butanamide (Compound 40).

In one embodiment of the invention, the compound of Formula I, a racemate or optical isomer, a pharmaceutically acceptable salt, a solvate, or a hydrate thereof according to the first aspect of the invention, is selected from the group consisting of:

3-chloro-N-(2-oxo-oxazolidin-3-yl)benzamide (Compound 5);
3-methyl-N-(2-oxo-oxazolidin-3-yl)benzamide (Compound 8);
4-fluoro-N-(2-oxo-oxazolidin-3-yl)benzamide (Compound 9);
2-trifluoromethyl-N-(2-oxo-oxazolidin-3-yl)benzamide (Compound 10);
2-(4-fluorophenyl)-N-(2-oxo-oxazolidin-3-yl)acetamide (Compound 31);
2-(4-methoxyphenyl)-N-(2-oxo-oxazolidin-3-yl)acetamide (Compound 32);
2-(4-nitrophenyl)-N-(2-oxo-oxazolidin-3-yl)acetamide (Compound 33);
2-(4-chlorophenyl)-N-(2-oxo-oxazolidin-3-yl)acetamide (Compound 34);
2-(4-tolyl)-N-(2-oxo-oxazolidin-3-yl)acetamide (Compound 35);
2-(4-nitrophenyl)-N-(2-oxo-oxazolidin-3-yl)propanamide (Compound 36);
2-(4-phenyl)-N-(2-oxo-oxazolidin-3-yl)propanamide (Compound 37);
2-(4-methylphenyl)-N-(2-oxo-oxazolidin-3-yl)propanamide (Compound 38);
2-(4-chlorophenyl)-N-(2-oxo-oxazolidin-3-yl)propanamide (Compound 39); and
N-(2-oxo-oxazolidin-3-yl)-4-phenyl butanamide (Compound 40).

In one embodiment of the invention, the compound of Formula I, a racemate or optical isomer, a pharmaceutically acceptable salt, a solvate, or a hydrate thereof according to the first aspect of the invention, is selected from the group consisting of:
4-tert-butyl-N-(2-oxo-oxazolidin-3-yl)benzamide (Compound 2);
4-chloromethyl-N-(2-oxo-oxazolidin-3-yl)benzamide (Compound 3);
4-nitro-N-(2-oxo-oxazolidin-3-yl)benzamide (Compound 7);
4-ethyl-N-(2-oxo-oxazolidin-3-yl)benzamide (Compound 11);
1-(2-oxo-oxazolidin-3-yl)-3-heptyl urea (Compound 18); and
1-(2-oxo-oxazolidin-3-yl)-3-octyl urea (Compound 19).

In a second aspect, the invention provides a method for preparing the compound of Formula I according to the first aspect of the invention, comprising the following steps of: reacting the intermediate 2 with acyl chloride represented by

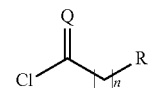

or isocyanate represented by

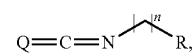

to prepare the compound of Formula I,

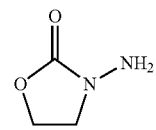

Intermediate 2

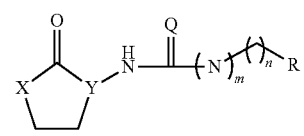

I wherein m, n, R, and Q are defined as they are in the first aspect of the invention.

In one embodiment of the invention, in the method according to the second aspect of the invention, the intermediate 2 is prepared from the reaction between 2-hydrazinoethanol and diethyl carbonate.

In one embodiment of the invention, in the method according to the second aspect of the invention, the reaction scheme is as follows:

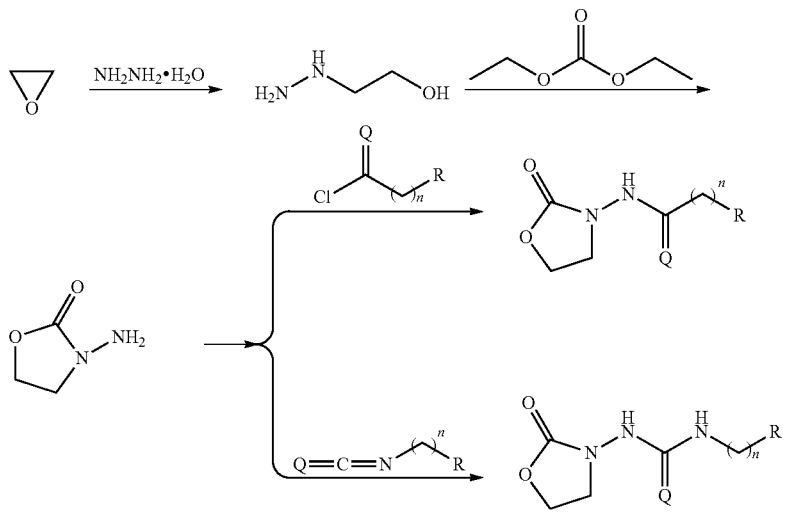

wherein Q, R, n are defined as they are in the first aspect of the invention.

In the third aspect, the invention provides a pharmaceutical composition, comprising the compound of Formula I, a racemate or optical isomer, a pharmaceutically acceptable salt, a solvate, or a hydrate thereof according to the first aspect of the invention, and optionally one or more pharmaceutically acceptable carrier or excipient.

The homoserinelactone derivative represented by Formula I according to the first aspect of the invention, a racemate or optical isomer, a pharmaceutically acceptable salt, a solvate, or a hydrate thereof, as a bacterial quorum-sensing regulator, may be used in combination with antibiotics, to enhance sensitivity of pathogenic bacteria to antibiotics. Thus, in one embodiment of the invention, the pharmaceutical composition according to the third aspect of the invention, may further comprise one or more antibiotics.

In the fourth aspect, the invention provides use of the compound of Formula I, a racemate or optical isomer, a pharmaceutically acceptable salt, a solvate, or a hydrate thereof according to the first aspect of the invention in the preparation of a medicament as a bacterial quorum-sensing regulator.

In the fifth aspect, the invention provides use of the pharmaceutical composition according to the third aspect of the invention in the preparation of a medicament as a bacterial quorum-sensing regulator.

In one embodiment of the invention, the use according to the fourth or fifth aspect of the invention, wherein said bacterial quorum-sensing regulator may be a bacterial quorum sensing agonist, or a bacterial quorum sensing inhibitor.

Specifically, in one embodiment of the invention, the compound of Formula I, a racemate or optical isomer, a pharmaceutically acceptable salt, a solvate, or a hydrate thereof selected from the following group, may be used in the preparation of a medicament as a bacterial quorum sensing agonist, 3-chloro-N-(2-oxo-oxazolidin-3-yl)benzamide (Compound 5);
3-methyl-N-(2-oxo-oxazolidin-3-yl)benzamide (Compound 8);
4-fluoro-N-(2-oxo-oxazolidin-3-yl)benzamide (Compound 9);
2-trifluoromethyl-N-(2-oxo-oxazolidin-3-yl)benzamide (Compound 10);
2-(4-fluorophenyl)-N-(2-oxo-oxazolidin-3-yl)acetamide (Compound 31);
2-(4-methoxyphenyl)-N-(2-oxo-oxazolidin-3-yl)acetamide (Compound 32);
2-(4-nitrophenyl)-N-(2-oxo-oxazolidin-3-yl)acetamide (Compound 33);
2-(4-chlorophenyl)-N-(2-oxo-oxazolidin-3-yl)acetamide (Compound 34);
2-(4-tolyl)-N-(2-oxo-oxazolidin-3-yl)acetamide (Compound 35);
2-(4-nitrophenyl)-N-(2-oxo-oxazolidin-3-yl)propanamide (Compound 36);
2-(4-phenyl)-N-(2-oxo-oxazolidin-3-yl)propanamide (Compound 37);
2-(4-methylphenyl)-N-(2-oxo-oxazolidin-3-yl)propanamide (Compound 38);
2-(4-chlorophenyl)-N-(2-oxo-oxazolidin-3-yl)propanamide (Compound 39); and
N-(2-oxo-oxazolidin-3-yl)-4-phenyl butanamide (Compound 40).

Specifically, in one embodiment of the invention, the compound of Formula I, a racemate or optical isomer, a pharmaceutically acceptable salt, a solvate, or a hydrate thereof, selected from the following group, may be used in the preparation of a medicament as a bacterial quorum sensing inhibitor, 4-tert-butyl-N-(2-oxo-oxazolidin-3-yl)benzamide (Compound 2);
4-chloromethyl-N-(2-oxo-oxazolidin-3-yl)benzamide (Compound 3);
4-nitro-N-(2-oxo-oxazolidin-3-yl)benzamide (Compound 7);
4-ethyl-N-(2-oxo-oxazolidin-3-yl)benzamide (Compound 11);
1-(2-oxo-oxazolidin-3-yl)-3-heptyl urea (Compound 18); and
1-(2-oxo-oxazolidin-3-yl)-3-octyl urea (Compound 19).

The compound of Formula I, a racemate or optical isomer, a pharmaceutically acceptable salt, a solvate, or a hydrate thereof according to the first aspect of the invention, as a bacterial quorum-sensing regulator, can inhibit or agonize bacterial quorum sensing, does not interfere with normal physiological functions of cells in vivo, and thus is regarded as new direction for the development of antibacterials. Particularly, the derivatives as bacterial quorum sensing inhibitors can be used in combination with antibiotics, to enhance sensitivity of pathogenic bacteria to antibiotics, and can be used to treat a disease or infection (including, but not limited to peritonitis, cholecystitis, cystitis, diarrhea, endocarditis, gastroenteritis, pyothorax, sepsis and other various diseases,) caused by a Gram-negative bacterium including, but not limited to *E. coli, Bacillus proteus, Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shigella* spp., *Pasteurella, Vibrio cholerae*, and *Vibrio Parahemolyticus*, particularly, to treat a disease caused by drug-resistant Gram-negative bacteria not sensitive to current antibiotics.

Therefore, in the sixth aspect, the invention provides use of the compound of Formula I, a racemate or optical isomer, a pharmaceutically acceptable salt, a solvate, or a hydrate thereof according to the first aspect of the invention in the preparation of a medicament for prevention and/or treatment of diseases caused by bacterial quorum sensing.

In the seventh aspect, the invention provides use of the pharmaceutical composition according to the third aspect of the invention in the preparation of a medicament for prevention and/or treatment of a disease caused by bacterial quorum sensing.

In the use according to the sixth aspect or the seventh aspect of the invention, the disease caused by a bacterial infection includes, but is not limited to an infection or disease (including, but not limited to peritonitis, cholecystitis, cystitis, diarrhea, endocarditis, gastroenteritis, pyothorax, sepsis and other various diseases) caused by a Gram-negative bacterium such as *E. coli, Bacillus proteus. Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shigella* spp., *Pasteurella, Vibrio cholerae*, and *Vibrio Parahemolyticus*, particularly, a disease caused by drug-resistant Gram-negative bacteria not sensitive to current antibiotics.

In the eighth aspect, the invention provides use of the compound of Formula I, a racemate or optical isomer, a pharmaceutically acceptable salt, a solvate or a hydrate thereof according to the first aspect of the invention as a tool drug for studying bacterial quorum sensing regulation.

DETAILED DESCRIPTION OF THE INVENTION

The terms and phrases used in the invention have the general meanings well known by a person skilled in the art, however, if they are specifically defined herein, the meanings defined herein shall prevail.

As used herein, the term "alkyl" has the general meanings well known in the art, and generally includes linear or branched alkyl. For example, the "alkyl" described in the invention may be C1-C9 alkyl, C1-C5 alkyl or C1-C4 alkyl. The C1-C9 alkyl, C1-C5 alkyl or C1-C4 alkyl refers to alkyl containing 1 to 9, 1 to 5, or 1 to 4 (including end values) carbon atoms, respectively. The "alkyl" described in the invention includes, but is not limited to methyl, ethyl, propyl, isopropyl, n-butyl, sec-butyl, tert-butyl, pentyl, hexyl, etc.

As used herein, the term "halogen" has the general meanings well known in the art, and generally includes F, Cl, Br, I, as well as their isotopes, and are preferably F, Cl and Br in the invention.

As used herein, the term "alkoxyl" has the general meanings well known in the art, and generally includes linear or branched alkoxyl. For example, the "alkoxyl" described in the invention may be C1-C6 alkoxyl, C1-C5 alkoxyl or C1-C4 alkoxyl. Said C1-C6 alkoxyl, C1-C5 alkoxyl or C1-C4 alkoxyl refers to alkoxyl containing 1 to 6, 1 to 5, or 1 to 4 (including end values) carbon atoms, respectively.

As used herein, the groups represented by the following terms have the general meanings well known in the art: nitrile group, trifluoromethyl, trifluoromethoxyl, hydroxyl, nitro, alkoxyl, and cyano.

As used herein, the terms "racemate" or "optical isomer" have the general meanings well known in the art.

According to the invention, the compounds of Formula I can be prepared by the following typical and exemplified method, comprising the following steps of:

1) putting 85% hydrazine hydrate in a three-neck flask in a −10° C. ethanol bath under stirring until hydrazine hydrate cools, slowly adding ethylene oxide dropwise, reacting for 1 hour and then slowly heating to 40° C., performing the reaction for a further hour, and distilling the reaction solution under reduced pressure to get colorless oily liquid (Intermediate 1);

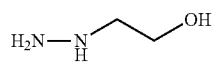

1

2) adding Intermediate 1, diethyl carbonate, and sodium methoxide to a three-necked flask, refluxing for 4 hours, cooling to precipitate solid, filtrating under vacuum, and recrystallizing in ethanol to get white solid (Intermediate 2).

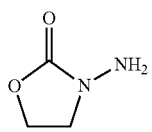

2

3) putting Intermediate 2 in a three-necked flask, adding water/dichloromethane, slowly adding dropwise acyl chloride represented by

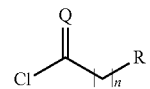

at room temperature, stirring overnight, precipitating white precipitates, filtrating under vacuum, subjecting the mother solution to column chromatography, and recrystallizing in ethanol, to get white solid (Compound of Formula 4).

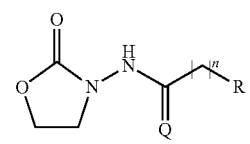

4

Wherein R and n are defined as they are in the Formula I of claim 1;

4) putting Intermediate 2 in a three-necked flask, adding 1,2-dimethoxyethane, slowly adding isocyanate represented by

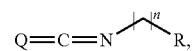

and then heating and refluxing for 15 mins, filtrating under vacuum, recrystallizing in isopropanol, to get white solid (Compound of Formula 5)

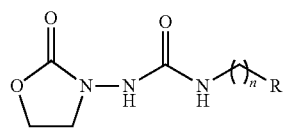

5

Wherein R, n, and Q are defined as they are in the first aspect of the invention.

BENEFICIAL EFFECTS OF THE INVENTION

The invention synthesizes a class of new bacterial quorum-sensing regulators represented by Formula I, which do not interfere with normal physiological functions of cells in vivo, and thus are regarded as new direction for the development of antibacterials, wherein the bacterial quorum-sensing inhibitors can be used in combination with antibiotics, to treat a infection or disease (including, but not limited to peritonitis, cholecystitis, cystitis, diarrhea, endocarditis, gastroenteritis, pyothorax, sepsis and other various diseases) caused by a Gram-negative bacterium including, but not limited to *E. coli, Bacillus proteus, Bacillus dysenteriae, Bacillus pneumoniae, Brucella, Haemophilus influenzae, Hemophilus parainfluenzae, Moraxella catarrhalis, Acinetobacter, Yersinia, legionella pneumophila, Bordetella pertussis, Bordetella parapertussis, Shigella* spp., *Pasteurella, Vibrio cholerae*, and *Vibrio Parahemolyticus*, particularly, to treat a disease caused by drug-resistant Gram-negative bacteria not sensitive to current antibiotics.

SPECIFIC MODES FOR CARRYING OUT THE INVENTION

The invention is further described by the following intermediates and examples. However, it should be understood that these intermediates and examples are only used to describe the invention more detailedly, and should not be understood as restricting the invention in any manner.

The invention describes the materials and experimental methods used in the experiments generally and/or in detail. Although many materials and methods used to achieve the purpose of the invention are well known in the art, the invention still describes them as detailedly as possible. A person skilled in the art knows that unless otherwise specified, the materials and methods used in the invention are well known in the art.

In the following examples, the melting points of the compounds were measured by YRT-3 type melting point apparatus, wherein the temperature was not calibrated. The specific rotatory power was measured by Polaar 3005 type Accuracy Automatic Polarimeter from OA Company. $^1$H-NMR spectra were measured by Bruker ARX 400 type NMR spectrometer. FAB mass spectra were measured by Zabspect High Resolution mass spectrometer.

Preparation of Intermediates

[Preparation of Intermediate 1] 2-hydrazinoethanol

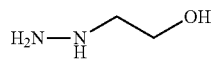

Intermediate 1

200 ml (4.12 mol) 85% hydrazine hydrate was put in a 500 ml three-necked flask in a −10 ethanol bath, under stirring until hydrazine hydrate cooled, 20 ml (0.39 mol) ethylene oxide was added slowly dropwise; after conducting the reaction for 1 hour, the temperature was increased to 40 slowly; the reaction was further carried out for 1 hour, and the reaction solution was distilled under reduced pressure at 155-160 (32 mmHg) to get 20 ml colorless oily liquid (Intermediate 1), with a yield of 67%.
$^1$H-NMR (400 MHz, D2O) δ ppm: 3.56 (2H, m), 2.73 (2H, m); EI-MS (m/z): 77.1 [M+H]+.

[Preparation of Intermediate 2] 3-amino oxazolidinone

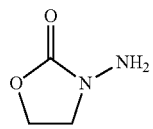

Intermediate 2

15.2 g (0.2 mol) 2-hydrazinoethanol (Intermediate 1), 31.0 g (0.2 mol) diethyl carbonate, and 3.0 g (57 mmol) sodium methoxide were added to a 100 ml three-necked flask, and were refluxed for 4 hours, and after cooling, solids were precipitated, filtrated under vacuum, and dried. The solvent in the mother solution was removed by distillation. After column chromatography (eluent: methanol/dichloromethane (at a ratio of 1:20 by volume)), the obtained white solid and the dried solid were recrystallized in ethanol, to get 15.3 g product (Intermediate 2), with a yield of 75%.
$^1$H-NMR (400 MHz, D2O) δ ppm: 4.33 (2H, t, J=8.0 Hz, J=8.0 Hz), 3.94 (2H, s), 3.70 (2H, t, J=4.0 Hz, J=4.0 Hz); EI-MS (m/z): 103.1 [M+H]+; m.p. 64-66.

EXAMPLES

[Example 1] 4-fluoro-N-(2-oxo-oxazolidin-3-yl) benzamide (Compound 1)

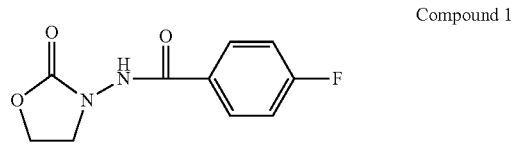 [SMILES: O=C(NN1CCOC1=O)c1ccc(F)cc1]

Compound 1

0.5 g (4.9 mmol) 3-amino oxazolidinone was put in a 25 ml three-necked flask, 10 ml water was added, and 0.92 g (5.9 mmol) 4-fluorobenzoyl chloride was added slowly dropwise at room temperature, the reaction system was stirred overnight. White precipitate was precipitated, filtrated under vacuum, and recrystallized in ethanol to get white solid (Compound 1) 0.61 g, with a yield of 56%.
$^1$H-NMR (400 MHz, DMSO) δ ppm: 10.87 (1H, s), 7.97 (2H, t, J=4.0 Hz, J=4.0 Hz), 7.40 (2H, t, J=8.0 Hz, J=12.0 Hz), 4.46 (2H, t, J=8.0 Hz, J=8.0 Hz), 3.79 (2H, t, J=8.0 Hz, J=8.0 Hz); EI-MS (m/z): 225.1 [M+H]+; m.p. 189-192.

[Example 2] 4-tert-butyl-N-(2-oxo-oxazolidin-3-yl) benzamide (Compound 2)

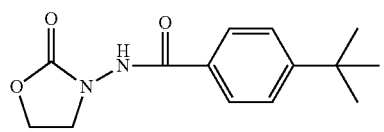

Compound 2

Intermediate 2 and 4-tert-butyl benzoyl chloride were used as raw materials, and operations were performed as they were in Example 1, to get white solid product (Compound 2).
$^1$H-NMR (400 MHz, DMSO) δ ppm: 10.74 (1H, s), 7.82 (2H, d, J=8.0 Hz), 7.55 (2H, d, J=8.0 Hz), 4.46 (2H, t, J=8.0 Hz, J=8.0 Hz), 3.77 (2H, t, J=8.0 Hz, J=8.0 Hz), 1.30 (9H, s); EI-MS (m/z): 263.3 [M+H]+; m.p. 187-189.

[Example 3] 4-chloromethyl-N-(2-oxo-oxazolidin-3-yl)benzamide (Compound 3)

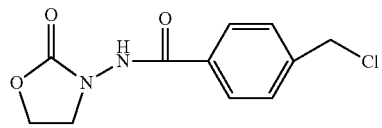

Compound 3

Intermediate 2 and 4-chloromethyl benzoyl chloride were used as raw materials, and operations were performed as they were in Example 1, to get white solid product (Compound 3).

$^1$H-NMR (400 MHz, DMSO) δ ppm: 10.86 (1H, s), 7.89 (2H, d, J=8.0 Hz), 7.60 (2H, d, J=8.0 Hz), 4.84 (2H, s), 4.46 (2H, t, J=8.0 Hz, J=8.0 Hz), 3.80 (2H, t, J=8.0 Hz, J=8.0 Hz); EI-MS (m/z): 255.1 [M+H]+; m.p. 206-208.

[Example 4] 2-chloro-N-(2-oxo-oxazolidin-3-yl) benzamide (Compound 4)

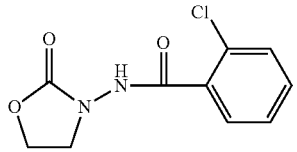

Compound 4

Intermediate 2 and 2-chlorobenzoyl chloride were used as raw materials, and operations were performed as they were in Example 1, to get white solid product (Compound 4).

$^1$H-NMR (400 MHz, DMSO) δ ppm: 10.75 (1H, s), 7.56 (4 Hm), 4.46 (2H, t, J=8.0 Hz, J=8.0 Hz), 3.79 (2H, t, J=8.0 Hz, J=8.0 Hz); EI-MS (m/z): 241.2 [M+H]+; m.p. 166-168.

[Example 5] 3-chloro-N-(2-oxo-oxazolidin-3-yl) benzamide (Compound 5)

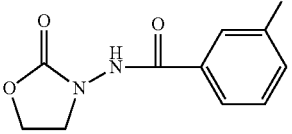

Compound 5

Intermediate 2 and 3-chlorobenzoyl chloride were used as raw materials, and operations were performed as they were in Example 1, to get white solid product (Compound 5).

$^1$H-NMR (400 MHz, DMSO) δ ppm: 10.96 (1H, s), 7.91 (1H, m), 7.85 (1H, d, J=8.0 Hz), 7.83 (H, d, J=8.0 Hz), 7.58 (1H, t, J=8.0 Hz, J=8.0 Hz), 4.47 (2H, t, J=8.0 Hz, J=8.0 Hz), 3.77 (2H, t, J=8.0 Hz, J=8.0 Hz); EI-MS (m/z): 241.2 [M+H]+; m.p. 151-152.

[Example 6] 2-fluoro-N-(2-oxo-oxazolidin-3-yl) benzamide (Compound 6)

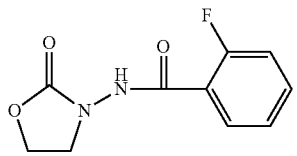

Compound 6

Intermediate 2 and 2-fluorobenzoyl chloride were used as raw materials, and operations were performed as they were in Example 1, to get white solid product (Compound 6).

$^1$H-NMR (400 MHz, DMSO) δ ppm: 10.62 (1H, s), 6.76 (2H, m), 6.36 (2H, m), 4.45 (2H, t, J=4.0 Hz, J=8.0 Hz), 3.79 (2H, t, J=4.0 Hz, J=8.0 Hz); EI-MS (m/z): 225.3 [M+H]+; m.p. 124-127.

[Example 7] 4-nitro-N-(2-oxo-oxazolidin-3-yl)benzamide (Compound 7)

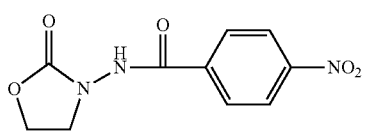

Compound 7

Intermediate 2 and 4-nitrobenzoyl chloride were used as raw materials, and operations were performed as they were in Example 1, to get white solid product (Compound 7).

$^1$H-NMR (400 MHz, DMSO) δ ppm: 11.18 (1H, s), 8.39 (2H, d, J=8.0 Hz), 8.12 (2H, d, J=8.0 Hz), 4.49 (2H, t, J=8.0 Hz, J=8.0 Hz), 3.82 (2H, t, J=8.0 Hz, J=8.0 Hz); EI-MS (m/z): 252.2 [M+H]+; m.p. 206-208.

[Example 8] 3-methyl-N-(2-oxo-oxazolidin-3-yl) benzamide (Compound 8)

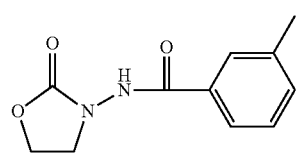

Compound 8

Intermediate 2 and 3-methyl benzoyl chloride were used as raw materials, and operations were performed as they were in Example 1, to get white solid product (Compound 8).

$^1$H-NMR (400 MHz, DMSO) δ ppm: 10.76 (1H, s), 7.69 (2H, m), 7.42 (2H, m), 4.46 (2H, t, J=8.0 Hz, J=8.0 Hz), 3.79 (2H, t, J=8.0 Hz, J=8.0 Hz), 2.37 (3H, s); EI-MS (m/z): 221.2 [M+H]+; m.p. 148-150.

[Example 9] 4-fluoro-N-(2-oxo-oxazolidin-3-yl) benzamide (Compound 9)

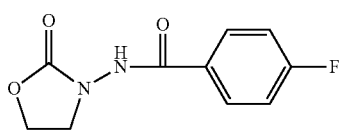

Compound 9

Intermediate 2 and 4-fluorobenzoyl chloride were used as raw materials, and operations were performed as they were in Example 1, to get white solid product (Compound 9).

$^1$H-NMR (400 MHz, DMSO) δ ppm: 10.87 (1H, s), 7.97 (2H, t, J=4.0 Hz, J=4.0 Hz), 7.40 (2H, t, J=8.0 Hz, J=12.0 Hz), 4.46 (2H, t, J=8.0 Hz, J=8.0 Hz), 3.79 (2H, t, J=8.0 Hz, J=8.0 Hz); EI-MS (m/z): 225.1 [M+H]+; m.p. 189-192.

[Example 10] 2-trifluoromethyl-N-(2-oxo-oxazolidin-3-yl)benzamide (Compound 10)

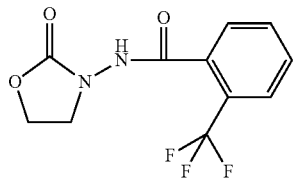

Compound 10

Intermediate 2 and 2-trifluoromethyl benzoyl chloride were used as raw materials, and operations were performed as they were in Example 1, to get white solid product (Compound 10).

$^1$H-NMR (400 MHz, DMSO) δ ppm: 10.86 (1H, s), 7.85 (1H, m), 7.81 (1H, m), 7.62 (1H, m), 7.60 (1H, m), 4.46 (2H, t, J=8.0 Hz, J=8.0 Hz), 3.77 (2H, t, J=8.0 Hz, J=8.0 Hz); EI-MS (m/z): 275.2 [M+H]+; m.p. 139-141.

[Example 11] 4-ethyl-N-(2-oxo-oxazolidin-3-yl)benzamide (Compound 11)

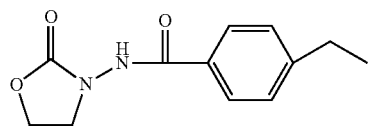

Compound 11

Intermediate 2 and 4-ethyl benzoyl chloride were used as raw materials, and operations were performed as they were in Example 1, to get white solid product (Compound 11).

$^1$H-NMR (400 MHz, DMSO) δ ppm: 10.74 (1H, s), 7.81 (2H, d, J=8.0 Hz), 7.37 (2H, d, J=8.0 Hz), 4.64 (2H, t, J=8.0 Hz, J=8.0 Hz), 3.79 (2H, m, J=8.0 Hz, J=8.0 Hz), 2.50 (2H, dd, J=4.0 Hz, J=4.0 Hz), 1.22 (3H, m); EI-MS (m/z): 235.1 [M+H]+; m.p. 170-173.

[Example 12] 4-bromo-N-(2-oxo-oxazolidin-3-yl)benzamide (Compound 12)

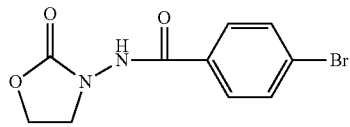

Compound 12

Intermediate 2 and 4-bromobenzoyl chloride were used as raw materials, and operations were performed as they were in Example 1, to get white solid product (Compound 12).

$^1$H-NMR (400 MHz, DMSO) δ ppm: 10.93 (1H, s), 7.83 (2H, d, J=8.0 Hz), 7.77 (2H, d, J=8.0 Hz), 4.46 (2H, t, J=8.0 Hz, J=8.0 Hz), 3.79 (2H, t, J=8.0 Hz, J=8.0 Hz); EI-MS (m/z): 285.1 [M+H]; m.p. 202-204.

[Example 13] 3-fluoro-N-(2-oxo-oxazolidin-3-yl)benzamide (Compound 13)

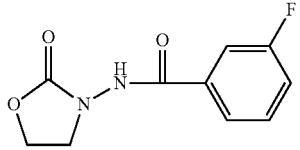

Compound 13

Intermediate 2 and 3-fluorobenzoyl chloride were used as raw materials, and operations were performed as they were in Example 1, to get white solid product (Compound 13).

$^1$H-NMR (400 MHz, DMSO) δ ppm: 10.94 (1H, s), 7.75 (1H, m), 7.68 (1H, m), 7.60 (1H, m), 7.59 (1H, m), 4.45 (2H, t, J=8.0 Hz, J=8.0 Hz), 3.78 (2H, t, J=8.0 Hz, J=8.0 Hz); EI-MS (m/z): 225.3 [M+H]+; m.p. 166-169.

[Example 14] 3-propyl-N-(2-oxo-oxazolidin-3-yl)benzamide (Compound 14)

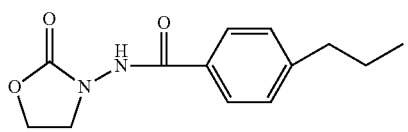

Compound 14

Intermediate 2 and 3-propyl benzoyl chloride were used as raw materials, and operations were performed as they were in Example 1, to get white solid product (Compound 14).

$^1$H-NMR (400 MHz, DMSO) δ ppm: 10.74 (1H, s), 7.81 (2H, d, J=8.0 Hz), 7.35 (2H, d, J=8.0 Hz), 4.44 (2H, t, J=8.0 Hz, J=8.0 Hz), 3.77 (2H, t, J=8.0 Hz, J=8.0 Hz), 2.13 (2H, t, J=8.0 Hz, J=8.0 Hz), 1.62 (2H, t, J=8.0 Hz, J=8.0 Hz), 0.88 (2H, t, J=8.0 Hz, J=4.0 Hz); EI-MS (m/z): 249.1 [M+H]+; m.p. 170-172.

[Example 15] 1-(2-oxo-oxazolidin-3-yl)-3-butyl urea (Compound 15)

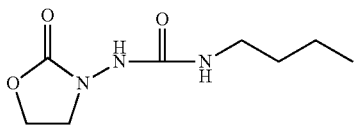

Compound 15

0.5 g (4.9 mmol) 3-amino oxazolidinone was put in a 25 ml three-necked flask, 10 ml 1,2-dimethoxyethane was added, and 1.2 g (5.9 mmol) n-butyl isocyanate was slowly added dropwise, and then after 30 mins, white solid was precipitated, and the mixture was heated under refluxing for 15 mins, filtrated under vacuum, and recrystallized in isopropanol, to get 0.61 g white solid (Compound 15), with a yield of 62%.

$^1$H-NMR (400 MHz, DMSO) δ ppm: 8.01 (1H, s), 6.69 (1H, s), 4.30 (2H, t, J=8.0 Hz, J=8.0 Hz), 3.59 (2H, t, J=8.0

Hz, J=8.0 Hz), 3.00 (2H, m), 1.37 (2H, m), 1.25 (2H, m), 0.87 (3H, m); EI-MS (m/z): 202.2 [M+H]+; m.p. 98-100.

[Example 16] 1-(2-oxo-oxazolidin-3-yl)-3-pentyl urea Compound 16)

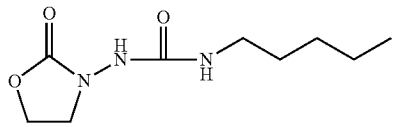

Compound 16

Intermediate 2 and pentyl isocyanate were used as raw materials, and operations were performed as they were in Example 15, to get white solid product (Compound 16).

¹H-NMR (400 MHz, DMSO) δ ppm: 8.01 (1H, s), 6.69 (1H, s), 4.30 (2H, t, J=8.0 Hz, J=8.0 Hz), 3.59 (2H, t, J=8.0 Hz, J=8.0 Hz), 2.99 (2H, m), 1.39 (2H, m), 1.25 (4H, m), 0.86 (3H, m); EI-MS (m/z): 216.3 [M+H]+; m.p. 83-86.

[Example 17] 1-(2-oxo-oxazolidin-3-yl)-3-hexyl urea (Compound 17)

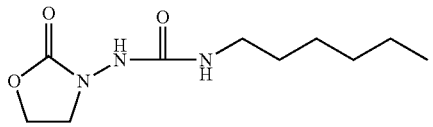

Compound 17

Intermediate 2 and hexyl isocyanate were used as raw materials, and operations were performed as they were in Example 15, to get white solid product (Compound 17).

¹H-NMR (400 MHz, DMSO) δ ppm: 8.02 (1H, s), 6.709 (1H, s), 4.30 (2H, t, J=8.0 Hz, J=8.0 Hz), 3.59 (2H, t, J=8.0 Hz, J=8.0 Hz), 2.99 (2H, m), 1.36 (8H, m), 0.86 (3H, m); EI-MS (m/z): 230.3 [M+H]+; m.p. 74-75.

[Example 18] 1-(2-oxo-oxazolidin-3-yl)-3-heptyl urea (Compound 18)

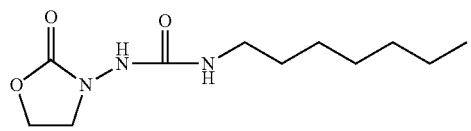

Compound 18

Intermediate 2 and heptyl isocyanate were used as raw materials, and operations were performed as they were in Example 15, to get white solid product (Compound 18).

¹H-NMR (400 MHz, DMSO) δ ppm: 8.01 (1H, s), 6.68 (1H, s), 4.30 (2H, t, J=8.0 Hz, J=8.0 Hz), 3.58 (2H, t, J=12.0 Hz, J=4.0 Hz), 2.99 (2H, m), 1.38 (2H, m), 1.28 (8H, m), 0.86 (3H, m); EI-MS (m/z): 244.3 [M+H]+; m.p. 68-69.

[Example 19] 1-(2-oxo-oxazolidin-3-yl)-3-octyl urea (Compound 19)

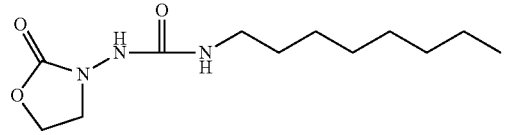

Compound 19

Intermediate 2 and octyl isocyanate were used as raw materials, and operations were performed as they were in Example 15, to get white solid product (Compound 19).

¹H-NMR (400 MHz, DMSO) δ ppm: 8.01 (1H, s), 6.68 (1H, s), 4.30 (2H, t, J=8.0 Hz, J=8.0 Hz), 3.59 (2H, t, J=8.0 Hz, J=8.0 Hz), 2.98 (2H, m), 1.38 (2H, m), 1.28 (10H, m), 0.86 (3H, m); EI-MS (m/z): 258.3 [M+H]+; m.p. 64-65.

[Example 20] 1-(4-bromophenyl)-3-(2-oxo-oxazolidin-3-yl)urea (Compound 20)

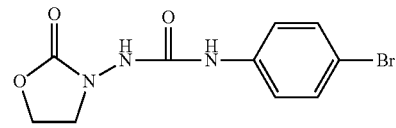

Compound 20

Intermediate 2 and 1-bromo-4-phenyl isocyanate were used as raw materials, and operations were performed as they were in Example 15, to get white solid product (Compound 20).

¹H-NMR (400 MHz, DMSO) δ ppm: 9.15 (1H, s), 8.54 (1H, s), 7.45 (4H, m), 4.37 (2H, t, J=8.0 Hz, J=8.0 Hz), 3.68 (2H, t, J=8.0 Hz, J=8.0 Hz); EI-MS (m/z): 302.3 [M+H]+; m.p. 212-215.

[Example 21] 1-(2-oxo-oxazolidin-3-yl)-3-p-tolylurea (Compound 21)

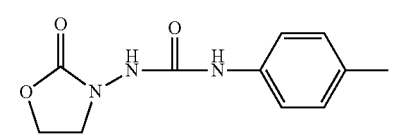

Compound 21

Intermediate 2 and 1-isocyanato-4-toluene were used as raw materials, and operations were performed as they were in Example 15, to get white solid product (Compound 21).

¹H-NMR (400 MHz, DMSO) δ ppm: 8.88 (1H, s), 8.37 (1H, s), 7.35 (2H, d, J=8.0 Hz), 7.08 (2H, d, J=8.0 Hz), 4.36 (2H, d, J=8.0H, J=8.0 Hz), 3.68 (2H, t, J=8.0 Hz, J=8.0 Hz), 2.23 (3H, s). EI-MS (m/z): 236.2 [M+H]+; m.p. 205-207.

[Example 22] 1-cyclohexyl-3-(2-oxo-oxazolidin-3-yl)urea (Compound 22)

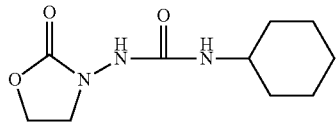

Compound 22

Intermediate 2 and cyclohexyl isocyanate were used as raw materials, and operations were performed as they were in Example 15, to get white solid product (Compound 22).

$^1$H-NMR (400 MHz, DMSO) δ ppm: 7.92 (1H, s), 6.49 (1H, d, J=8.0 Hz), 4.30 (2H, t, J=8.0 Hz, J=8.0 Hz), 3.59 (2H, t, J=8.0 Hz, J=8.0 Hz), 1.71 (5H, m), 1.17 (5H, m); EI-MS (m/z): 228.2[M+H]+; m.p. 203-205.

[Example 23] 1-benzyl-3-(2-oxo-oxazolidin-3-yl)urea (Compound 23)

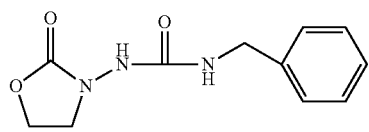

Compound 23

Intermediate 2 and isocyanatomethyl-benzene were used as raw materials, and operations were performed as they were in Example 15, to get white solid product (Compound 23).

$^1$H-NMR (400 MHz, DMSO) δ ppm: 8.21 (1H, s), 7.30 (6H, m), 4.31 (2H, t, J=8.0 Hz, J=-4.0 Hz), 4.23 (2H, d, J=8.0 Hz), 3.62 (2H, t, J=8.0 Hz, J=8.0 Hz); EI-MS (m/z): 236.2 [M+H]+; m.p. 160-161.

[Example 24] 1-(2-oxo-oxazolidin-3-yl)phenyl ethyl urea (Compound 24)

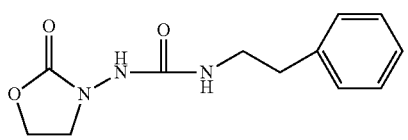

Compound 24

Intermediate 2 and isocyanatomethyl-benzene were used as raw materials, and operations were performed as they were in Example 15, to get white solid product (Compound 24).

$^1$H-NMR (400 MHz, DMSO) δ ppm: 8.12 (1H, s), 7.29 (2H, m), 7.22 (3H, t, m), 6.79 (1H, s), 4.30 (2H, t, J=8.0 Hz), 3.59 (2H, t, J=4.0 Hz, J=8.0 Hz), 3.23 (2H, m), 2.71 (2H, t, J=4.0 Hz, J=8.0 Hz); EI-MS (m/z): 250.3 [M+H]+; m.p. 123-125.

[Example 25] 1-(2-oxo-oxazolidin-3-yl)-3-(m-tolyl)urea (Compound 25)

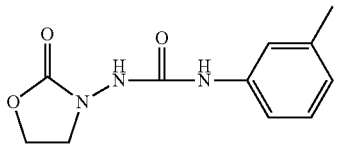

Compound 25

Intermediate 2 and 1-isocyanato-3-toluene were used as raw materials, and operations were performed as they were in Example 15, to get white solid product (Compound 25).

$^1$H-NMR (400 MHz, DMSO) δ ppm: 8.90 (1H, s), 8.39 (1H, s), 7.30 (2H, m), 7.14 (1H, t, J=8.0 Hz, J=8.0 Hz), 6.81 (2H, d, J=8.0 Hz), 4.36 (2H, t, J=8.0 Hz, J=8.0 Hz), 3.69 (2H, t, J=4.0 Hz, J=8.0 Hz). EI-MS (m/z): 236.2 [M+H]+; m.p. 191-192.

[Example 26] 1-(3-bromophenyl)-3-(2-oxo-oxazolidin-3-yl)urea (Compound 26)

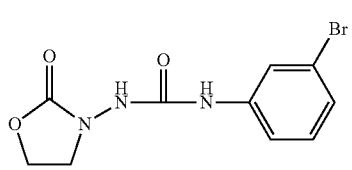

Compound 26

Intermediate 2 and 1-bromo-3-phenyl isocyanate were used as raw materials, and operations were performed as they were in Example 15, to get white solid product (Compound 26).

$^1$H-NMR (400 MHz, DMSO) δ ppm: 9.20 (1H, s), 8.61 (1H, s), 7.82 (2H, s), 7.42 (1H, s), 7.17 (2H, m), 4.37 (2H, t, J=8.0 Hz, J=8.0 Hz), 3.68 (2H, t, J=8.0 Hz, J=4.0 Hz). EI-MS (m/z): 301.1 [M+H]+; m.p. 197-199.

[Example 27] 1-(2-oxo-oxazolidin-3-yl)phenylthiourea (Compound 27)

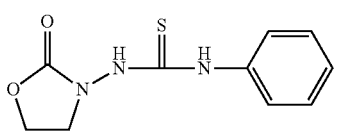

Compound 27

Intermediate 2 and phenyl isothiocyanate were used as raw materials, and operations were performed as they were in Example 15, to get white solid product (Compound 27).

$^1$H-NMR (400 MHz, DMSO) δ ppm: 10.10 (1H, s), 9.69 (1H, s), 7.47 (2H, d, J=8.0 Hz), 7.36 (2H, t, J=8.0 Hz, J=8.0 Hz), 7.20 (1H, t, J=8.0 Hz, J=8.0 Hz), 4.41 (2H, m), 3.62 (2H, m). EI-MS (m/z): 238.2 [M+H]+; m.p. 191-193.

[Example 28] 1-(4-fluorophenyl)-3-(2-oxo-oxazolidin-3-yl)sulfourea (Compound 28)

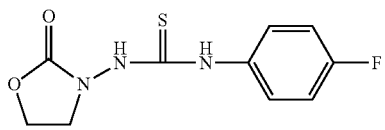

Compound 28

Intermediate 2 and 1-fluoro-4-phenyl isothiocyanate were used as raw materials, and operations were performed as they were in Example 15, to get white solid product (Compound 28).

$^1$H-NMR (400 MHz, DMSO) δ ppm: 10.10 (1H, s), 9.73 (1H, s), 7.45 (2H, m), 7.20 (2H, t, J=8.0 Hz, J=8.0 Hz), 4.39 (2H, m), 3.79 (2H, m). EI-MS (m/z): 256.2 [M+H]+; m.p. 190-191.

[Example 29] 1-(3-bromophenyl)-3-(2-oxo-oxazolidin-3-yl)urea (Compound 29)

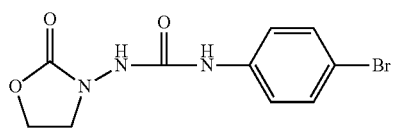

Compound 29

Intermediate 2 and 1-bromo-4-phenyl isocyanate were used as raw materials, and operations were performed as they were in Example 15, to get white solid product (Compound 29).

$^1$H-NMR (400 MHz, DMSO) δ ppm: 9.20 (1H, s), 8.61 (1H, s), 7.82 (H, s), 7.42 (H, s), 7.17 (2H, m), 4.37 (2H, t, J=8.0 Hz, J=8.0 Hz), 3.68 (2H, t, J=8.0 Hz, J=4.0 Hz). EI-MS (m/z): 302.1 [M+H]+; m.p. 212-215.

[Example 30] 1-(2-oxo-oxazolidin-3-yl)-3-(4-trifluoromethoxyphenyl)urea (Compound 30)

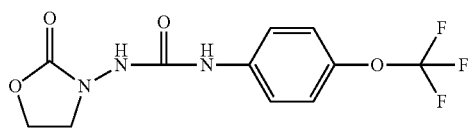

Compound 30

Intermediate 2 and 1-isocyanato-4-trifluoromethoxy-benzene were used as raw materials, and operations were performed as they were in Example 15, to get white solid product (Compound 30).

$^1$H-NMR (400 MHz, DMSO) δ ppm: 9.21 (1H, s), 8.55 (1H, s), 7.59 (2H, d, J=8.0 Hz), 7.29 (2H, d, J=8.0 Hz), 4.37 (2H, t, J=8.0 Hz, J=8.0 Hz), 3.69 (2H, t, J=8.0 Hz, J=8.0 Hz). EI-MS (m/z): 306.1 [M+H]+; m.p. 205-206.

[Example 31] 2-(4-fluorophenyl)-N-(2-oxo-oxazolidin-3-yl)acetamide (Compound 31)

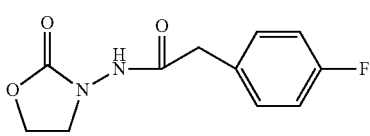

Compound 31

0.5 g (4.9 mmol) 3-amino oxazolidinone (Intermediate 2) was added to a 50 ml three-necked flask, 25 ml dichloromethane and 0.75 g (7.4 mmol) triethylamine were added, and 1.0 g (5.9 mmol) 2-(4-fluorophenyl) acetyl chloride was slowly added dropwise at 0 in an ice bath, and then the mixture was stirred at room temperature overnight, the solvent was distilled under reduced pressure, and the residue was recrystallized in ethanol, to get 0.52 g white solid (Compound 31), with a yield of 45%.

$^1$H-NMR (400 MHz, DMSO) δ ppm: 10.41 (1H, s), 7.30 (2H, t, J=4.0 Hz, J=8.0 Hz), 7.17 (2H, t, J=8.0 Hz, J=8.0 Hz), 4.35 (2H, t, J=8.0 Hz, J=8.0 Hz), 3.65 (2H, t, J=8.0 Hz, J=8.0 Hz), 3.49 (2H, s); EI-MS (m/z): 239.2 [M+H]+; m.p. 131-134.

[Example 32] 2-(4-methoxyphenyl)-N-(2-oxo-oxazolidin-3-yl)acetamide (Compound 32)

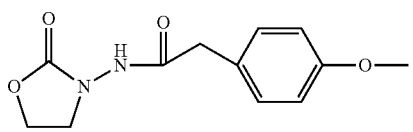

Compound 32

Intermediate 2 and 2-(4-methoxyphenyl)acetyl chloride were used as raw materials, and operations were performed as they were in Example 31, to get white solid product (Compound 32).

$^1$H-NMR (400 MHz, DMSO) δ ppm: 10.35 (1H, s), 7.20 (2H, d, J=8.0 Hz), 6.88 (2H, d, J=8.0 Hz), 4.35 (2H, t, J=8.0 Hz, J=8.0 Hz), 3.73 (3H, s), 3.63 (2H, t, J=4.0 Hz, J=8.0 Hz), 3.40 (2H, m). EI-MS (m/z): 251.2 [M+H]+; m.p. 90-92.

[Example 33] 2-(4-nitrophenyl)-N-(2-oxo-oxazolidin-3-yl)acetamide (Compound 33)

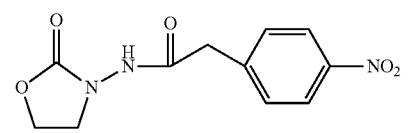

Compound 33

Intermediate 2 and 2-(4-nitrophenyl)acetyl chloride were used as raw materials, and operations were performed as they were in Example 31, to get white solid product (Compound 33).

$^1$H-NMR (400 MHz, DMSO) δ ppm: 10.52 (1H, s), 8.20 (2H, d, J=8.0 Hz), 7.57 (2H, d, J=8.0 Hz), 4.36 (2H, t, J=8.0 Hz, J=8.0 Hz), 3.68 (4H, m); EI-MS (m/z): 266.2 [M+H]+; m.p. 180-183.

[Example 34] 2-(4-chlorophenyl)-N-(2-oxo-oxazolidin-3-yl)acetamide (Compound 34)

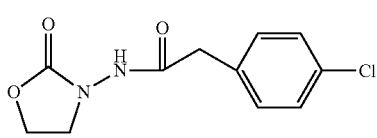

Compound 34

Intermediate 2 and 2-(4-chlorophenyl)acetyl chloride were used as raw materials, and operations were performed as they were in Example 31, to get white solid product (Compound 34).

$^1$H-NMR (400 MHz, DMSO) δ ppm: 10.42 (1H, s), 7.40 (2H, d, J=8.0 Hz), 7.31 (2H, d, J=8.0 Hz), 4.35 (2H, t, J=8.0 Hz, J=8.0 Hz), 3.65 (2H, t, J=8.0 Hz, J=8.0 Hz), 3.50 (2H, s); EI-MS (m/z): 255.6 [M+H]+; m.p. 124-127.

[Example 35] 2-(4-tolyl)-N-(2-oxo-oxazolidin-3-yl) acetamide (Compound 35)

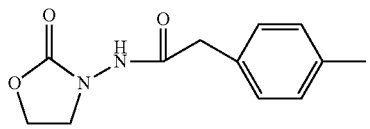

Compound 35

Intermediate 2 and 2-(4-tolyl)acetyl chloride were used as raw materials, and operations were performed as they were in Example 31, to get white solid product (Compound 35).

$^1$H-NMR (400 MHz, DMSO) δ ppm: 10.37 (1H, s), 7.13 (4H, m), 4.35 (2H, t, J=8.0 Hz, J=8.0 Hz), 3.63 (2H, t, J=8.0 Hz, J=8.0 Hz), 3.43 (2H, s), 2.27 (3H, s). EI-MS (m/z): 235.2 [M+H]+; m.p. 108-111.

[Example 36] 2-(4-nitrophenyl)-N-(2-oxo-oxazolidin-3-yl)propanamide (Compound 36)

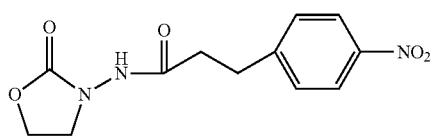

Compound 36

Intermediate 2 and 3-(4-nitrophenyl)propionyl chloride were used as raw materials, and operations were performed as they were in Example 31, to get white solid product (Compound 36).

$^1$H-NMR (400 MHz, DMSO) δ ppm: 10.21 (1H, s), 8.16 (2H, d, J=8.0 Hz), 7.54 (2H, d, J=12.0 Hz), 4.35 (2H, t, J=8.0 Hz, J=8.0 Hz), 3.61 (2H, t, J=8.0H, J=8.0 Hz), 2.99 (2H, t, J=4.0 Hz, J=8.0 Hz). EI-MS (m/z): 280.1 [M+H]+; m.p. 143-145.

[Example 37] 2-(4-phenyl)-N-(2-oxo-oxazolidin-3-yl)propanamide (Compound 37)

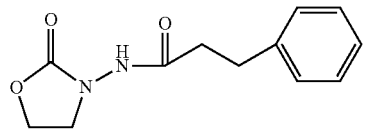

Compound 37

Intermediate 2 and 3-phenyl propionyl chloride were used as raw materials, and operations were performed as they were in Example 31, to get white solid product (Compound 37).

$^1$H-NMR (400 MHz, DMSO) δ ppm: 10.16 (1H, s), 7.26 (5H, m), 4.37 (2H, t, J=8.0 Hz, J=8.0 Hz), 3.61 (2H, t, J=8.0H, J=8.0 Hz), 2.83 (2H, t, J=4.0 Hz, J=8.0 Hz), 2.42 (2H, t, J=8.0 Hz, J=8.0 Hz). EI-MS (m/z): 280.1 [M+H]+; m.p. 150-152.

[Example 38] 2-(4-methylphenyl)-N-(2-oxo-oxazolidin-3-yl)propanamide (Compound 38)

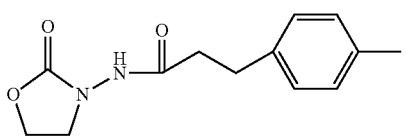

Compound 38

Intermediate 2 and 3-(4-methylphenyl) propionyl chloride were used as raw materials, and operations were performed as they were in Example 31, to get white solid product (Compound 38).

$^1$H-NMR (400 MHz, DMSO) δ ppm: 10.15 (1H, s), 7.09 (4H, m), 4.35 (2H, t, J=8.0 Hz, J=8.0 Hz), 3.63 (2H, t, J=8.0 Hz), 2.78 (2H, m), 2.41 (3H, t, J=8.0 Hz, J=8.0 Hz), 2.25 (3H, s). EI-MS (m/z): 249.4 [M+H]+; m.p. 146-148.

[Example 39] 2-(4-chlorophenyl)-N-(2-oxo-oxazolidin-3-yl)propanamide (Compound 39)

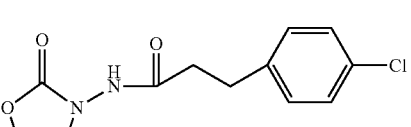

Compound 39

Intermediate 2 and 3-(4-methylphenyl) propionyl chloride were used as raw materials, and operations were performed as they were in Example 31, to get white solid product (Compound 39).

$^1$H-NMR (400 MHz, DMSO) δ ppm: 10.16 (1H, s), 732 (4H, m), 4.35 (2H, t, J=8.0 Hz, J=8.0 Hz), 3.61 (2H, t, J=8.0

Hz, J=8.0 Hz), 2.83 (2H, t, J=8.0 Hz, J=8.0 Hz), 2.44 (2H, t, J=8.0 Hz, J=8.0 Hz); EI-MS (m/z): 269.2 [M+H]+; m.p. 134-136.

[Example 40] N-(2-oxo-oxazolidin-3-yl)-4-phenyl butanamide (Compound 40)

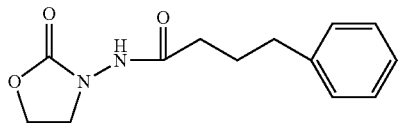

Compound 40

Intermediate 2 and 4-phenyl butyryl chloride were used as raw materials, and operations were performed as they were in Example 31, to get white solid product (Compound 40).
$^1$H-NMR (400 MHz, DMSO) δ ppm: 10.12 (1H, s), 7.27 (2H, m), 7.20 (2H, m), 4.35 (2H, t, J=8.0 Hz, J=7.6 Hz), 3.65 (2H, t, J=8.0 Hz, J=8.0 Hz), 2.577 (2H, m), 2.4 (2H, t, J=8.0 Hz, J=8.0 Hz), 1.81 (2H, m): EI-MS (m/z): 249.3 [M+H]+; m.p. 104-107.

[Experimental Example] Evaluation of Activity of the Bacterial Quorum-Sensing Regulators According to the Invention The activity of the bacterial quorum-sensing regulators according to the invention may be measured by the following methods.

1. Method for Preliminary Screening 1.1 Preparation work: different compounds to be tested (Compounds 1-40 prepared in Example 1-40) were weighted and then were dissolved in 200 μl DMSO (dimethyl sulfoxide) to prepare a solution at a concentration of 0.065M. 5.0 mg inducer, N-hexanoyl homoserine lactone ($C_6$-HSL, purchased from Sigma Company), was weighted and was dissolved in 200 μl DMSO (at a concentration of 0.125M), and the compounds and the inducer were stored at 4 for further use. C. violaceum CV026 (donated by Professor McLean J C from Texas State University) in LB culture medium (LB culture medium consisting of 1% (percentage by mass) tryptone, 0.5% (percentage by mass) yeast extract, 1% (percentage by mass) NaCl and water) was cultured under shaking in a shaker at 30, 200 rpm to get the culture medium for further use.

1.2 Method for preliminary screening of compounds having agonistic activity: 400 μl C. violaceum CV026 (at a bacterial concentration of 1×10$^8$/ml) was added to 5 ml melted semi-solid LB culture medium, and was mixed well; the mixed culture medium was poured into a solid LB plate; when the mixed culture medium was solidified on the plate, lattice was made thereon; 1 μl of the dissolved compounds to be tested (Compounds 1-40 in Examples 1-40, at a concentration of 0.065M) was spotted on the plate; when the compounds on the plate was dried in air, the plate was put in a 30° C. oven upside down and was cultured for a period of 16-18 h. If the compound to be tested has an agonistic effect on C. violaceum CV026 on the LB plate, purple stain will be induced on the LB plate. The agonistic activity of a compound is determined depending on whether purple stain is induced for C. violaceum CV026 on LB plate as well as the purple depth.

1.3 Method for preliminary screening of compounds having inhibitory activity: the inducer $C_6$-HSL was diluted gradiently to 1000 times by means of 2-fold dilution; 15 μl diluted inducer and 400 μl C. violaceum CV026 in exponential phase (at a bacterial concentration of 1×10$^8$/ml) were mixed well and then were added to a 5 ml melted semi-solid LB culture medium; the mixture of inducer, C. violaceum, and semi-solid LB was poured onto a solid LB plate; when the mixture was solidified on the plate, lattice was made thereon: 1 μl of the dissolved compounds to be tested (Compounds 1-40 in Examples 1-40, at a concentration of 0.065M) was spotted on the plate; when the compounds on the plate were dried in air, the plate was put in a 30° C. oven upside down and was cultured for a period of 16-18 h. If the compound to be tested has an inhibitory effect on C. violaceum CV026 on the LB plate, white circle will appear on the LB plate. The inhibitory activity of a compound is preliminary determined depending on the size of the white circle appeared after C. violaceum CV026 was inhibited on LB plate.

It is found after preliminary screening that 22 compounds according to the invention have bacterial quorum sensing regulatory activity, and the screening result was shown in Table 1.

2. Measurement of $IC_{50}$ of Compounds Having an Inhibitory Effect on C. violaceum Quorum Sensing 2.1 The wells of a 12-well plate were marked as initial concentration, 2, 4, 8, 16, 32, 64, 128, 256, DMSO group, and a blank control group from left to right and from up to bottom, respectively.

2.2 The monoclonal C. violaceum CV026 grew on LB solid plate was cultured to exponational phase in a 5 ml fresh LB liquid culture medium, 50 μl was then taken for seeding in a 5 ml LB culture medium, and was cultured until the optical density OD value was about 1.0 at 585 nm; the culture was then mixed well with LB culture medium at a ratio of 1:9 by volume (with OD of about 0.15), and was added to a 12-well plate in an amount of 2 ml/well.

2.3 The compounds preliminarily screened to have quorum sensing inhibitory activity were dissolved respectively in DMSO (at a concentration of 0.065M), and then 10 μl was taken into 10 μl DMSO solution to achieve the purpose of 2-fold dilution, and so on. Each compound was gradiently diluted to a highest fold of 256 (gradient dilution of 2, 4, 8, 16, 32, 64, 128, 256 fold).

2.4 To each well, 15 μl 1000-fold diluted inducer C6-HSL (initial concentration of 0.125M) and 8 μl compound solution at each diluted gradient was added; to DMSO control group, 8 μl DMSO was added; to a blank control group, 8 μl LB culture medium was added. Finally, it was ensured that 2 ml culture in each of the 12-well plate was mixed well.

2.5 The 12-well plate was placed in a 30° C. shaker at 130 rpm and was cultured for 10-12 h.

2.6 After the culture was finished, 1 ml culture was taken from each well and was put in a 1.5 ml EP tube and then was centrifugated at 12000 rpm for 10 mins. The supernatant of the culture was sucked out, and 500 μl DMSO was added to each EP tube to dissolve the purple pigment in the culture. After the pigment was completely dissolved, centrifugation was performed at 12000 rpm for 10 mins. 200 μl supernatant pigment was put in a 96-well culture plate, and was measured for absorbance value at 585 nm by a Microplate Reader, and the absorbance value was measured at 585 nm by a microplate reader, the absorbance value and the corresponding concentration were plotted to get the $IC_{50}$ value. The specific results are shown in Table 2.

TABLE 1

Screening result of bacterial quorum sensing regulatory activity

| Compound No. | Regulatory activity | Compound No. | Regulatory activity |
|---|---|---|---|
| 2 | − | 3 | − |
| 4 | ± | 5 | + |
| 7 | − | 8 | + |
| 9 | + | 10 | + |
| 11 | − | 12 | ± |
| 18 | − | 19 | − |
| 31 | + | 32 | + |
| 33 | + | 34 | + |
| 35 | + | 36 | + |
| 37 | + | 38 | + |
| 39 | + | 40 | + |

In Table 1,
"+" represents that a compound has bacterial quorum sensing agonistic activity,
"−" represents that a compound has bacterial quorum sensing inhibitory activity, and
"±" represents that a compound has both agonistic and inhibitory activity on the bacterial quorum sensing.

TABLE 2

$IC_{50}$ value (μM) of compounds having bacterial quorum sensing inhibitory activity

| Compound No. | $IC_{50}$ | Compound No. | $IC_{50}$ |
|---|---|---|---|
| 7 | 18.67 ± 2.59 | 11 | 13.90 ± 4.21 |
| 12 | 7.85 ± 1.71 | | |

The experiments on evaluation of activity of said bacterial quorum-sensing regulators demonstrated that compounds of Formula I according to the invention, particularly Compound 1-6, 9, 12, 14-17, 20, 22-24 and 27-28 had a regulatory effect on bacterial quorum sensing, wherein Compound 2, 3, 7, 11, 18, and 19 had an inhibitory effect on bacterial quorum sensing, while Compound 5, 8, 9, 10, and 31-40 had an agonizing effect on bacterial quorum sensing, and Compound 4 and 12 had both an agonizing effect and an inhibitory effect on bacterial quorum sensing.

To sum up, the invention synthesizes a class of new bacterial quorum-sensing regulators represented by Formula I, which do not interfere with normal physiological functions of cells in vivo, and thus are regarded as new direction for the development of antibacterials, wherein the bacterial quorum-sensing inhibitors can be used in combination with antibiotics, to treat an infection or disease (including, but not limited to peritonitis, cholecystitis, cystitis, diarrhea, endocarditis, gastroenteritis, pyothorax, sepsis and other various diseases) caused by a Gram-negative bacterium including, but not limited to *E. coli*, *Bacillus proteus*, *Bacillus dysenteriae*, *Bacillus pneumoniae*, *Brucella*, *Haemophilus influenzae*, *Hemophilus parainfluenzae*, *Moraxella catarrhalis*, *Acinetobacter*, *Yersinia*, *legionella pneumophila*, *Bordetella pertussis*, *Bordetella parapertussis*, *Shigella* spp., *Pasteurella*, *Vibrio cholerae*, and *Vibrio Parahemolyticus*, particularly, a disease caused by drug-resistant Gram-negative bacteria not sensitive to current antibiotics.

The invention claimed is:

1. A compound of Formula I, a racemate or optical isomer, a pharmaceutically acceptable salt, a solvate, or a hydrate thereof,

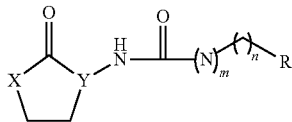

wherein
(1) X is O; Y is N; Q is O or S;
   m is 1;
   n is an integer of from 0 to 9;
   R is cyclohexyl or a substituted phenyl ring; wherein the phenyl ring is mono-substituted or multi-substituted by a substituent selected from the group consisting of: substituted or unsubstituted C1-C5 linear or branched alkyl, halogen, cyano, trifluoromethyl, hydroxyl, nitro, and substituted or unsubstituted C1-C5 alkoxyl; or
(2) X is O; Y is N; Q is O or S;
   m is 0;
   n is an integer of from 1 to 9; and
   R is cyclohexyl or a substituted phenyl ring; wherein the phenyl ring is mono-substituted or multi-substituted by a substituent selected from the group consisting of: substituted or unsubstituted C1-C5 linear or branched alkyl, halogen, cyano, trifluoromethyl, hydroxyl, nitro, and substituted or unsubstituted C1-C5 alkoxyl.

2. The compound, a racemate or optical isomer, a pharmaceutically acceptable salt, a solvate, or a hydrate thereof according to claim 1, wherein
(1) X is O, Y is N, and Q is O,
   m is 0,
   n is an integer of from 1 to 9, and
   R is a substituted phenyl ring; wherein the phenyl ring is mono-substituted or multi-substituted by a substituent selected from the group consisting of: substituted or unsubstituted C1-C5 linear or branched alkyl, halogen, cyano, trifluoromethyl, hydroxyl, nitro, and substituted or unsubstituted C1-C5 alkoxyl; or
(2) X is O, Y is N, and Q is O or S,
   m is 1,
   n is an integer of from 1 to 9, and
   R is cyclohexyl or a substituted phenyl ring; wherein the phenyl ring is mono-substituted or multi-substituted by a substituent selected from the group consisting of: substituted or unsubstituted C1-C5 linear or branched alkyl, halogen, cyano, trifluoromethyl, trifluoromethoxyl, phenyl, hydroxyl, nitro, and substituted or unsubstituted C1-C5 alkoxyl.

3. A compound, a racemate or optical isomer, a pharmaceutically acceptable salt, a solvate, or a hydrate thereof, selected from the group consisting of:
   4-fluoro-N-(2-oxo-oxazolidin-3-yl) benzamide (Compound 1);
   4-tert-butyl-N-(2-oxo-oxazolidin-3-yl) benzamide (Compound 2);
   4-chloromethyl-N-(2-oxo-oxazolidin-3-yl) benzamide (Compound 3);
   2-chloro-N-(2-oxo-oxazolidin-3-yl) benzamide (Compound 4);
   3-chloro-N-(2-oxo-oxazolidin-3-yl) benzamide (Compound 5);
   2-fluoro-N-(2-oxo-oxazolidin-3-yl) benzamide (Compound 6);
   4-nitro-N-(2-oxo-oxazolidin-3-yl) benzamide (Compound 7);

3-methyl-N-(2-oxo-oxazolidin-3-yl) benzamide (Compound 8);
4-fluoro-N-(2-oxo-oxazolidin-3-yl) benzamide (Compound 9);
2-trifluoromethyl-N-(2-oxo-oxazolidin-3-yl) benzamide (Compound 10);
4-ethyl-N-(2-oxo-oxazolidin-3-yl) benzamide (Compound 11);
4-bromo-N-(2-oxo-oxazolidin-3-yl) benzamide (Compound 12);
3-fluoro-N-(2-oxo-oxazolidin-3-yl) benzamide (Compound 13);
3-propyl-N-(2-oxo-oxazolidin-3-yl) benzamide (Compound 14);
1-(2-oxo-oxazolidin-3-yl)-3-butyl urea (Compound 15);
1-(2-oxo-oxazolidin-3-yl)-3-pentyl urea (Compound 16);
1-(2-oxo-oxazolidin-3-yl)-3-hexyl urea (Compound 17);
1-(2-oxo-oxazolidin-3-yl)-3-heptyl urea (Compound 18);
1-(2-oxo-oxazolidin-3-yl)-3-octyl urea (Compound 19);
1-(4-bromophenyl)-3-(2-oxo-oxazolidin-3-yl) urea (Compound 20);
1-(2-oxo-oxazolidin-3-yl)-3-p-tolylurea (Compound 21);
1-cyclohexyl-3-(2-oxo-oxazolidin-3-yl) urea (Compound 22);
1-benzyl-3-(2-oxo-oxazolidin-3-yl) urea (Compound 23);
1-(2-oxo-oxazolidin-3-yl) phenyl ethyl urea (Compound 24);
1-(2-oxo-oxazolidin-3-yl)-3-(m-tolyl) urea (Compound 25);
1-(3-bromophenyl)-3-(2-oxo-oxazolidin-3-yl) urea (Compound 26);
1-(2-oxo-oxazolidin-3-yl) phenylthiourea (Compound 27);
1-(4-fluorophenyl)-3-(2-oxo-oxazolidin-3-yl) sulfourea (Compound 28);
1-(3-bromophenyl)-3-(2-oxo-oxazolidin-3-yl) urea (Compound 29);
1-(2-oxo-oxazolidin-3-yl)-3-(4-trifluoromethoxyphenyl) urea (Compound 30);
2-(4-fluorophenyl)-N-(2-oxo-oxazolidin-3-yl) acetamide (Compound 31);
2-(4-methoxyphenyl)-N-(2-oxo-oxazolidin-3-yl) acetamide (Compound 32);
2-(4-nitrophenyl)-N-(2-oxo-oxazolidin-3-yl) acetamide (Compound 33);
2-(4-chlorophenyl)-N-(2-oxo-oxazolidin-3-yl) acetamide (Compound 34);
2-(4-tolyl)-N-(2-oxo-oxazolidin-3-yl) acetamide (Compound 35);
2-(4-nitrophenyl)-N-(2-oxo-oxazolidin-3-yl) propanamide (Compound 36);
2-(4-phenyl)-N-(2-oxo-oxazolidin-3-yl) propanamide (Compound 37);
2-(4-methylphenyl)-N-(2-oxo-oxazolidin-3-yl) propanamide (Compound 38);
2-(4-chlorophenyl)-N-(2-oxo-oxazolidin-3-yl) propanamide (Compound 39); and
N-(2-oxo-oxazolidin-3-yl)-4-phenyl butanamide (Compound 40).

4. The compound, a racemate or optical isomer, a pharmaceutically acceptable salt, a solvate, or a hydrate thereof according to claim 3, selected from the group consisting of:
3-chloro-N-(2-oxo-oxazolidin-3-yl) benzamide (Compound 5);
3-methyl-N-(2-oxo-oxazolidin-3-yl) benzamide (Compound 8);
4-fluoro-N-(2-oxo-oxazolidin-3-yl) benzamide (Compound 9);
2-trifluoromethyl-N-(2-oxo-oxazolidin-3-yl) benzamide (Compound 10);
2-(4-fluorophenyl)-N-(2-oxo-oxazolidin-3-yl) acetamide (Compound 31);
2-(4-methoxyphenyl)-N-(2-oxo-oxazolidin-3-yl) acetamide (Compound 32);
2-(4-nitrophenyl)-N-(2-oxo-oxazolidin-3-yl) acetamide (Compound 33);
2-(4-chlorophenyl)-N-(2-oxo-oxazolidin-3-yl) acetamide (Compound 34);
2-(4-tolyl)-N-(2-oxo-oxazolidin-3-yl) acetamide (Compound 35);
2-(4-nitrophenyl)-N-(2-oxo-oxazolidin-3-yl) propanamide (Compound 36);
2-(4-phenyl)-N-(2-oxo-oxazolidin-3-yl) propanamide (Compound 37);
2-(4-methylphenyl)-N-(2-oxo-oxazolidin-3-yl) propanamide (Compound 38);
2-(4-chlorophenyl)-N-(2-oxo-oxazolidin-3-yl) propanamide (Compound 39); and
N-(2-oxo-oxazolidin-3-yl)-4-phenyl butanamide (Compound 40).

5. The compound, a racemate or optical isomer, a pharmaceutically acceptable salt, a solvate, or a hydrate thereof according to claim 3, selected from the group consisting of:
4-tert-butyl-N-(2-oxo-oxazolidin-3-yl) benzamide (Compound 2);
4-chloromethyl-N-(2-oxo-oxazolidin-3-yl) benzamide (Compound 3);
4-nitro-N-(2-oxo-oxazolidin-3-yl) benzamide (Compound 7); and
4-ethyl-N-(2-oxo-oxazolidin-3-yl) benzamide (Compound 11).

6. A pharmaceutical composition, comprising the compound of Formula I, a racemate or optical isomer, a pharmaceutically acceptable salt, a solvate, or a hydrate thereof according to claim 1, and optionally one or more pharmaceutically acceptable carriers or excipients.

7. The compound of Formula I, a racemate or optical isomer, a pharmaceutically acceptable salt, a solvate, or a hydrate thereof according to claim 4, which is used as a bacterial quorum sensing inhibitor.

8. The compound of Formula I, a racemate or optical isomer, a pharmaceutically acceptable salt, a solvate, or a hydrate thereof according to claim 5, which is used as a bacterial quorum sensing agonist.

9. The compound according to claim 1, a racemate or optical isomer, a pharmaceutically acceptable salt, a solvate, or a hydrate thereof, wherein
(1) X is O, Y is N, and Q is O,
m is 0,
n is 1, 2 or 3, and
R is a substituted phenyl ring, wherein the phenyl ring is mono-substituted or multi-substituted by a substituent selected from the group consisting of: halogen, trifluoromethyl, methyl, chloromethyl, nitro, ethyl, n-propyl, iso-propyl, and methoxyl; or
(2) X is O, Y is N, Q is O or S,
m is 1, n is 1, 2, 3, 4, 5, 6, 7 or 8, and
R is cyclohexyl, or a substituted phenyl ring, wherein the phenyl ring is mono-substituted or multi-substituted by a substituent selected from the group consisting of: halogen, trifluoromethyl, methyl, chloromethyl, nitro, ethyl, n-propyl, iso-propyl, methoxyl, and trifluoromethoxyl.

10. A compound of Formula I, a racemate or optical isomer, a pharmaceutically acceptable salt, a solvate, or a hydrate thereof,

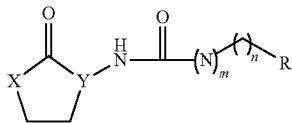

wherein
(1) X is O, Y is N, and Q is O,
   m is 0, n is an integer of 0-3, and R is a substituted-phenyl ring, wherein the phenyl ring is mono-substituted or multi substituted by a substituent selected from the group consisting of: F, Br, I, cyano and trifluoromethyl; or
(2) X is O, Y is N, and Q is O or S,
   m is 1, n is an integer of 0-3, and R is substituted or unsubstituted C1-C9 linear alkyl, branched alkyl or cycloalkyl; or a substituted phenyl ring, wherein the phenyl ring is mono-substituted or multi-substituted by a substituent selected from the group consisting of: substituted or unsubstituted linear or branched alkyl, halogen, cyano, trifluoromethyl, hydroxyl, nitro, and alkoxyl,
(3) X is O, Y is N, and Q is O,
   m is 0, n is 0 or 1, and
   R is a substituted phenyl ring, wherein the phenyl ring is mono-substituted or multi-substituted by a substituent selected from the group consisting of: F, Br, I, trifluoromethyl, chloromethyl, nitro, ethyl, n-propyl and iso-propyl; or
(4) X is O, Y is N, Q is O or S,
   m is 1, n is 0, and
   R is cyclohexyl or a substituted phenyl ring, wherein the phenyl ring is mono-substituted or multi-substituted by a substituent selected from the group consisting of: halogen, trifluoromethyl, methyl, chloromethyl, nitro, ethyl, n-propyl, iso-propyl, methoxyl, and trifluoromethoxyl; or
(5) X is O, Y is N, Q is O or S,
   m is 1, n is 1, 2, 3, 4, 5, 6, 7 or 8, and
   R is hydrogen, cyclohexyl, a substituted or unsubstituted phenyl ring, wherein the phenyl ring is optionally mono-substituted or multi-substituted by a substituent selected from the group consisting of: halogen, trifluoromethyl, methyl, chloromethyl, nitro, ethyl, n-propyl, iso-propyl, methoxyl and trifluoromethoxyl.

11. The compound, a racemate or optical isomer, a pharmaceutically acceptable salt, a solvate, or a hydrate thereof according to claim 10,
wherein
(1) X is O, Y is N, and Q is O,
   m is 0, n is an integer of 0-3, R is bromophenyl, fluorophenyl, nitrophenyl, cyanophenyl, methylphenyl, ethylphenyl, trifluoromethylphenyl, ethoxyphenyl, or halogenated methylphenyl; or
(2) X is O, Y is N, and Q is O or S,
   m is 1, n is an integer of 0-3, R is methyl, ethyl, propyl, butyl, pentyl, hexyl, cyclohexyl, heptyl, octyl, phenyl, chlorophenyl, bromophenyl, or methylphenyl.

12. The pharmaceutical composition according to claim 6, wherein the pharmaceutical composition may further comprise one or more antibiotics.

13. A pharmaceutical composition, comprising the compound of Formula I, a racemate or optical isomer, a pharmaceutically acceptable salt, a solvate, or a hydrate thereof according to claim 3, and optionally one or more pharmaceutically acceptable carriers or excipients.

14. A pharmaceutical composition, comprising the compound of Formula I, a racemate or optical isomer, a pharmaceutically acceptable salt, a solvate, or a hydrate thereof according to claim 10, and optionally one or more pharmaceutically acceptable carriers or excipients.

15. The compound, a racemate or optical isomer a pharmaceutically acceptable salt, a solvate, or a hydrate thereof of claim 3 selected from the group consisting of:
   4-tert-butyl-N-(2-oxo-oxazolidin-3-yl) benzamide (Compound 2);
   4-nitro-N-(2-oxo-oxazolidin-3-yl) benzamide (Compound 7);
   2-trifluoromethyl-N-(2-oxo-oxazolidin-3-yl) benzamide (Compound 10);
   3-propyl-N-(2-oxo-oxazolidin-3-yl) benzamide (Compound 14);
   1-(2-oxo-oxazolidin-3-yl)-3-butyl urea (Compound 15);
   1-(2-oxo-oxazolidin-3-yl)-3-pentyl urea (Compound 16);
   1-(2-oxo-oxazolidin-3-yl)-3-hexyl urea (Compound 17);
   1-(2-oxo-oxazolidin-3-yl)-3-heptyl urea (Compound 18);
   1-(2-oxo-oxazolidin-3-yl)-3-octyl urea (Compound 19);
   1-(2-oxo-oxazolidin-3-yl)-3-(4-trifluoromethoxyphenyl) urea (Compound 30);
   2-(4-nitrophenyl)-N-(2-oxo-oxazolidin-3-yl) acetamide (Compound 33);
   2-(4-nitrophenyl)-N-(2-oxo-oxazolidin-3-yl) propanamide (Compound 36);
   2-(4-phenyl)-N-(2-oxo-oxazolidin-3-yl) propanamide (Compound 37);
   2-(4-methylphenyl)-N-(2-oxo-oxazolidin-3-yl) propanamide (Compound 38);
   2-(4-chlorophenyl)-N-(2-oxo-oxazolidin-3-yl) propanamide (Compound 39); and
   N-(2-oxo-oxazolidin-3-yl)-4-phenyl butanamide (Compound 40).

16. A pharmaceutical composition, comprising the compound of claim 15, a racemate or optical isomer, a pharmaceutically acceptable salt, a solvate, or a hydrate thereof, and optionally one or more pharmaceutically acceptable carriers or excipients.

* * * * *